US006914137B2

(12) United States Patent
Baker

(10) Patent No.: US 6,914,137 B2
(45) Date of Patent: Jul. 5, 2005

(54) ISOLATION OF NUCLEIC ACIDS

(75) Inventor: Matthew John Baker, Maldstone (GB)

(73) Assignee: DNA Research Innovations Limited, Kent (GB)

( * ) Notice: Subject to any disclaimer, the term of this patent is extended or adjusted under 35 U.S.C. 154(b) by 0 days.

(21) Appl. No.: 09/736,632

(22) Filed: Dec. 14, 2000

(65) Prior Publication Data

US 2001/0018513 A1 Aug. 30, 2001

Related U.S. Application Data

(63) Continuation-in-part of application No. 09/586,009, filed as application No. PCT/GB98/03602 on Dec. 4, 1998.

(30) Foreign Application Priority Data

Dec. 6, 1997 (GB) .............................................. 9725839
Jul. 17, 1998 (GB) .............................................. 9815541

(51) Int. Cl.[7] .............................................. C07H 21/04
(52) U.S. Cl. ........................................ 536/25.4; 521/25
(58) Field of Search ............................ 536/25.4; 521/25

(56) References Cited

U.S. PATENT DOCUMENTS

| | | | |
|---|---|---|---|
| 4,843,012 A | 6/1989 | DeBonville et al. | |
| 4,908,318 A | 3/1990 | Lerner | |
| 4,921,805 A | 5/1990 | Gebeyehu et al. | |
| 4,923,978 A | 5/1990 | McCormick | |
| 5,057,426 A | 10/1991 | Henco et al. | |
| 5,124,444 A | 6/1992 | Van Ness et al. | |
| 5,128,247 A | 7/1992 | Koller | |
| 5,204,246 A | 4/1993 | Jhingan | |
| 5,234,809 A | 8/1993 | Boom et al. | |
| 5,334,499 A | 8/1994 | Burdick et al. | |
| 5,508,164 A | 4/1996 | Kausch et al. | |
| 5,512,439 A | * 4/1996 | Hornes et al. ................. | 435/6 |
| 5,596,092 A | 1/1997 | Schneider | |
| 5,599,667 A | * 2/1997 | Arnold et al. ................. | 435/6 |
| 5,612,473 A | 3/1997 | Wu et al. | |
| 5,622,822 A | 4/1997 | Ekeze et al. | |
| 5,631,146 A | 5/1997 | Szostak et al. | |
| 5,641,628 A | 6/1997 | Bianchi | |
| 5,652,348 A | * 7/1997 | Burton et al. ................. | 536/20 |
| 5,654,179 A | 8/1997 | Lin | |
| 5,660,984 A | 8/1997 | Davis et al. | |
| 5,705,628 A | 1/1998 | Hawkins | |
| 5,770,712 A | 6/1998 | Roy et al. | |
| 5,843,663 A | * 12/1998 | Stanley et al. ................. | 435/6 |
| 5,874,221 A | * 2/1999 | Tooley et al. ................. | 435/6 |
| 5,898,071 A | 4/1999 | Hawkins | |
| 5,916,746 A | * 6/1999 | Cobbs et al. ................. | 435/6 |
| 5,981,235 A | 11/1999 | Shultz et al. | |
| 6,051,380 A | 4/2000 | Sosnowski et al. | |
| 6,060,246 A | * 5/2000 | Summerton et al. ........... | 435/6 |
| 6,090,288 A | 7/2000 | Berglund et al. | |
| 6,194,562 B1 | 2/2001 | Smith et al. | |
| 6,270,970 B1 | 8/2001 | Smith et al. | |
| 6,284,470 B1 | 9/2001 | Bitner et al. | |
| 6,310,199 B1 | 10/2001 | Smith et al. | |
| 6,342,387 B1 | 1/2002 | Hayashizaki et al. | |
| 6,534,262 B1 | 3/2003 | McKernan et al. | |
| 6,562,573 B2 | 5/2003 | Halaka | |
| 2001/0041795 A1 | 11/2001 | Halaka | |
| 2002/0025572 A1 | 2/2002 | Hayashizaki et al. | |

FOREIGN PATENT DOCUMENTS

| | | |
|---|---|---|
| EP | 0 301 899 | 7/1988 |
| EP | 0 338 591 | 4/1989 |
| EP | 0 366 438 | 10/1989 |
| EP | 0 512 767 A1 | 11/1992 |
| EP | 0 515 484 B1 | 12/1992 |
| EP | 0 707 077 | 9/1995 |
| EP | 0 853 123 | 1/1997 |
| EP | 0 389 063 B1 | 8/1997 |
| EP | 0 832 897 | 9/1997 |
| EP | 0 834 729 | 9/1997 |
| EP | 0 897 978 | 8/1998 |
| GB | 2 282 138 | 9/1993 |
| WO | WO 90/08159 | 7/1990 |
| WO | WO 91/12079 | 8/1991 |
| WO | WO 93/03167 | 2/1993 |
| WO | WO 95/13368 | 5/1995 |
| WO | WO 95/27718 | 10/1995 |
| WO | WO 96/08500 | 3/1996 |
| WO | WO 96/09116 | 3/1996 |
| WO | WO 96/18732 | 6/1996 |
| WO | WO 96/36706 | 11/1996 |
| WO | WO 96/41810 | 12/1996 |
| WO | WO 97/10331 | 3/1997 |
| WO | WO 97/28171 | 8/1997 |
| WO | WO 97/29825 | 8/1997 |
| WO | WO 99/22021 | 5/1999 |
| WO | WO 00/44928 | 8/2000 |
| WO | WO 00/49031 | 8/2000 |
| WO | WO 00/65041 | 11/2000 |
| WO | WO 00/69872 | 11/2000 |
| WO | WO 00/70040 | 11/2000 |
| WO | WO 00/70041 | 11/2000 |
| WO | WO 02/10373 | 2/2002 |
| WO | WO 02/16580 | 2/2002 |

OTHER PUBLICATIONS

Reeck et al. Resultion of a spectrum of nucleoprotein species in sonicated chromatin. PNAS vol. 69:2317–2321, 1972.*

(Continued)

Primary Examiner—James Ketter
(74) Attorney, Agent, or Firm—Vinson & Elkins, LLP

(57) ABSTRACT

A method for extracting nucleic acids from a biological material such as blood comprises contacting the mixture with a material at a pH such that the material is positively charged and will bind negatively charged nucleic acids and then eluting the nucleic acids at a pH when the said materials possess a neutral or negative charge to release the nucleic acids. The nucleic acids can be removed under mildly alkaline conditions to the maintain integrity of the nucleic acids and to allow retrieval of the nucleic acids in reagents that are immediately compatible with either storage or analytical testing.

42 Claims, No Drawings

OTHER PUBLICATIONS

Peterson et al. Chromatographic isolation of 80s ribosomes from rat liver adn mouse plasma cell tumor. Biochemistry vol. 8(7):2916–2923, 1969.*

Kothari et al. RNA fractionation on modified celluses 1. Ecteola–, echam–, aminoethyl–, nucleic acid–, and nitrocellulose. J. Chromatography vol. 73:449–462, 1972.*

Sigma catalogue, pp. 1556–1560.*

"Fluka catalogue 1995/1996", XP–002205379, p. 354.

"Fluka catalogue 1995/1996", XP–002205380, p. 879.

Bitner, R. et al. "Use of MagneSil™ Paramagnetic Particles for Plasmid Purification, PCR Cleanup, and Purification of Dideoxy and Big Dye DNA Sequencing Reactions"; Proceedings of SPIE, 3926: 126–133 (2000).

McLaughlin, "Mixed–Mode Chromatography of Nucleic Acids"; Chem. Rev., 89: 309–19 (1989).

XP–002106739 Abstract of JP 98–210396.

English language abstract of EP 853,123.

Slaby, I. et al. "Rapid Isolation of Homogeneous Cloned T7 Gene 5 Protein and T7 DNA Polymerase by Affinity Chromotography"; Protein Expression and Purification 2: 270–277 (1991).

Li, F. et al. "Construction and Application of a Prokaryotic Vector which Expresses the Protein that Can be Quickly Purified by IMAC"; Chinese Journal of Biotechnology 13: 37–42 (1995).

Lu, T. et al. "Combined pH gradient and anion–exchange high–performance liquid chromatographic separation of oligodeoxyribonucleotides"; Journal of Chromatography A, 686: 339–343 (1994).

Millard, F. et al. "Fractionation of Mammalian DNA on DEAE–Cellulose"; Journal of Chromatography 107: 125–140 (1975).

Freidelder, D. "Chromatography"; Physical Biochemistry, 2nd Edition), Chapter 8 (1982).

Natarajan, G. et al. "Helix—Coil Transitions in DNA Using a pH Variation Method: Case of a Melting Paradox as a Function of Ionic Strength"; Analytical Biochemistry 237: 152–155 (1996).

de Latour and Kolm, *Magnetic Separation in Water Pollution Control* –11, IEEE Transactions on Magnetics, vol. Mag–11, No. 5, Sep. 1975.

Munro, et al., *Magnetic Seeding to Aid Recovery of Biological Precipitates*, Biotechnology Letters, vol. 3, No. 6, 297–302 (1981).

Gerald R. Reeck, et al., "Resolution of a Spectrum of Nucleoprotein Species in Sonicated Chromatin," *Proc. Nat. Acad. Sci. USA*, 69(8):2317–2321 (1972).

* cited by examiner

ISOLATION OF NUCLEIC ACIDS

This application is a continuation-in-part of U.S. Ser. No. 09/586,009, filed 2 Jun. 2000, which is a continuation of PCT/GB98/03602, filed 4 Dec. 1998, which claims priority from UK patent application numbers 9725839,6, filed 6 Dec. 1997, and 9815541.9, filed 17 Jul. 1998. The entire disclosure of the '009 application is incorporated by reference herein.

The present invention relates to a method for extracting nucleic acids and other biomolecules from biological materials, particularly blood and other liquid samples.

There is a very large demand for DNA analysis for a range of purposes and this has lead to the requirement for quick, safe, high throughput methods for the isolation and purification of DNA and other nucleic acids.

Samples for use for DNA identification or analysis can be taken from a wide range of sources such as biological material such as animal and plant cells, faeces, tissue etc. also samples can be taken from soil, foodstuffs, water etc.

Existing methods for the extraction of DNA include the use of phenol/chloroform, salting out, the use of chaotropic salts and silica resins, the use of affinity resins, ion exchange chromatography and the use of magnetic beads. Methods are described in U.S. Pat. Nos. 5,057,426, 4,923,978, EP Patents 0512767 A1 and EP 0515484B and WO 95/13368, WO 97/10331 and WO 96/18731. These patents and patent applications disclose methods of adsorbing nucleic acids on to a solid support and then isolating the nucleic acids. The previously used methods use some type of solvent to isolate the nucleic acids and these solvents are often flammable, combustible or toxic.

EP0707077A2 describes a synthetic water soluble polymer to precipitate nucleic acids at acid pH and release at alkaline pH. The re-dissolving of the nucleic acids is performed at extremes of pH, temperature and/or high salt concentrations where the nucleic acids, especially RNA, can become denatured, degraded or require further purification or adjustments before storage and analysis.

WO 96/09116 discloses mixed mode resins for recovering a target compound, especially a protein, from aqueous solution at high or low ionic strength, using changes in pH. The resins have a hydrophobic character at the pH of binding of the target compound and a hydrophilic and/or electrostatic character at the pH of desorption of the target compound.

Blood is one of the most abundant sample sources for DNA analysis as blood samples are routinely taken for a wide range of reasons. However because of the viscous and proteinaceous nature of blood using known DNA extraction methods it has proved difficult to accomplish using automation due to the difficulties of handling large volumes containing relatively small amounts of DNA. Hitherto nucleic acid extraction has been partially automated only by using hazardous reagents and slow processing times.

I have now devised an improved method for the extraction of nucleic acids and other biomolecules from blood and other biological materials, and other samples containing nucleic acid.

According to the invention there is provided a method for the extraction of biomolecules from biological material which method comprises contacting the biological material with a solid phase which is able to bind the biomolecules to it at a first pH and then extracting the biomolecules bound to the solid phase by elution using an elution solvent at a second pH.

In particular there is provided a method for extracting nucleic acid from a sample containing nucleic acid, which method comprises: contacting the sample with said solid phase at a first pH at which the solid phase has a positive charge and will bind negatively charged nucleic acid; and then releasing the nucleic acid at a higher pH at which the solid phase possesses a neutral, negative or less positive charge than at the first pH.

Generally the solid phase will possess an overall positive charge, that is the sum of all positive and negative charges on the solid phase as a whole is positive. It is possible (though not preferred), however, that the solid phase as a whole could be negatively charged, but have areas of predominantly positive charge to which the nucleic acid can bind. Such solid phases are within the scope of the invention.

The change in the charge of the solid phase is referred to herein as "charge switching" and is accomplished by the use of a "charge switch material" in, on or as the solid phase.

The charge switch material comprises an ionisable group, which changes charge to according to the ambient conditions. The charge switch material is chosen so that the pKa of the ionisable group is appropriate to the conditions at which it is desired to bind nucleic acid to and release nucleic acid from the solid phase. Generally, nucleic acid will be bound to the charge switch material at a pH below or roughly equal to the pKa, when the charge switch material is positively charged, and will be released at a higher pH (usually above the pKa), when the charge switch material is less positively charged, neutral, or negatively charged.

The present invention is more particularly directed to the use of charge switch materials which allow binding and/or releasing (especially releasing) of the nucleic acid to occur under mild conditions of temperature and/or pH and/or ionic strength.

Generally the charge switch material will change charge because of a change in charge on a positively ionisable group from positive to less positive or neutral, as the pH is increased in a range spanning or close to the pKa of the positively ionisable group. This may also be combined with a change of charge on a negatively ionisable group from neutral or less negative to more negative. In an alternative embodiment (described below), however, the charge switch material comprises a material which is positively charged at both pH values (such as a metal oxide) and a negatively ionisable group, the charge of which becomes more negative as the pH is increased in a range spanning or close to its pKa.

The charge switch material may comprise an ionisable group having a pKa between about 3 and 9. For positively ionisable groups, the pKa is more preferably at least about 4.5, 5.0, 5.5, 6.0 or 6.5 and/or at most about 8.5, 8.0, 7.5 or 7.0. A particularly preferred pKa for a positively ionisable group is between about 5 and 8; even more preferred is a pKa between about 6.0 and 7.0, more preferably between about 6.5 and 7.0. The pKa for negatively ionisable groups is preferably between about 3 and 7, still more preferably between about 4 and 6, further preferably approximately at the pH at which it is desired to bind nucleic acid.

Materials having more than one pKa value (e.g. having different ionisable groups), or combinations of materials having different pKa values, may also be suitable for use as charge switch materials in accordance with the invention, provided that at a first (lower) pH the material(s) possess(es) a positive charge and that at a higher pH the charge is less positive, neutral or negative.

Generally a charge switch will be achieved by changing the pH from a value below to a value above the pKa of the or an ionisable group. However, it will be appreciated that when the pH is the same as the pKa value of a particular ionisable group, 50% of the individual ionisable groups will be charged and 50% neutral. Therefore, charge switch effects can also be achieved by changing the pH in a range close to, but not spanning, the pKa of an ionisable group. For example, at the pKa of a negatively ionisable group, such as a carboxy group (pKa typically around 4), 50% of such groups will be in the ionised form (e.g. $COO^-$) and 50% in the neutral form (e.g. COOH). As the pH increases, an increasing proportion of the groups will be in the negative form.

Preferably the binding step is carried out at a pH of below the pKa of the ionisable group, or (though this is not preferred) within about 1 pH unit above the pKa. Generally the releasing step is carried out at a pH above the pKa of the ionisable group, preferably at a pH between 1 and 3 pH units above the pKa.

Prior art methods, such as those disclosed in EP0707077, often use high pH to release the nucleic acid, for example using strong bases such as NaOH. Such high pH can cause depurination of nucleic acid, leading to the problems of imperfect replication, which can impede subsequent use of the nucleic acid, e.g. in detection and/or amplification techniques such as Southern or northern blotting or PCR.

The use of strong bases, or weak bases in combination with heating, again as in EP0707077, can also lead to degradation of RNA (especially at pH values of 10 or above), and denaturation of double stranded DNA (i.e. irreversible conversion of DNA from the double stranded form at least partially into the single stranded form), which can lead to a lack of specific binding in PCR.

The appropriate choice of pKa value(s) in accordance with the invention allows the step of releasing DNA from the solid phase to be performed under mild conditions, unlike in the prior art. As used herein, the term "mild conditions" generally means conditions under which nucleic acid is not denatured and/or not degraded and/or not depurinated, and/or conditions which are substantially physiological.

Preferably the releasing step is performed at a pH of no greater than about pH 10.5, more preferably no greater than about pH 10.0, 9.8, 9.6, 9.4, 9.2, 9.0, 8.9, 8.8, 8.7, 8.6 or 8.5. Depending on the pKa(s) of the charge switch material, the releasing step may even be performed at lower pH values, such as 8.0, 7.5 or 7.0. Preferably the releasing step is carried out in the substantial absence of NaOH, preferably also the substantial absence of other alkali metal hydroxides, more preferably the substantial absence of strong mineral bases. Substantial absence may mean that the concentration is less than 25 mM, preferably less than 20 mM, more preferably less than 15 mM or 10 mM.

The desired change in pH can be achieved by altering the ionic strength of the solution and/or the temperature, since pH is dependent on both these factors. However, neither high temperature nor high ionic strength are generally compatible with the desired mild conditions, and accordingly, the change in pH is preferably not achieved by large changes in ionic strength or temperature. Moreover, increasing ionic strength increases competition of charged species with the nucleic acid for binding to the solid phase, so can assist in releasing the nucleic acid. Small changes of ionic strength are therefore acceptable and may be used in conjunction with the change in pH to release the nucleic acid, preferably within the limits and ranges given below.

Preferably the temperature at which the releasing step performed is no greater than about 70° C., more preferably no greater than about 65° C., 60° C., 55° C., 50° C., 45° C. or 40° C. More preferably, such temperatures apply to the entire process. The releasing step, or the entire process, may even be performed at lower temperatures, such as 35° C., 30° C. or 25° C.

Furthermore, the releasing step preferably occurs under conditions of low ionic strength, suitably less than 1M or 500 mM, preferably less than 400 mM, 300 mM, 200 mM, 100 mM, 75 mM, 50 mM, 40 mM, 30 mM, 25 mM, 20 mM or 15 mM. It may even be below 10 mM. The ionic strength may be at least about 5 mM, more preferably at least about 10 mM. More preferably, these ionic strengths also apply to the binding step.

PCR is sensitive to pH and the presence of charged contaminants. In particularly preferred embodiments, the releasing step is performed using reagents suitable for storing nucleic acid (such as a commercially available storage buffer, e.g. 10 mM Tris.HCl, pH8.0–8.5, optionally in the presence of 1 mM EDTA), or using reagents suitable for use in a procedure to which the nucleic acid is to be subjected (such as a PCR buffer, e.g. 10 mM Tris.HCl, 50 mM KCl, pH 8.5).

Common previously known nucleic acid extraction processes require a step of diluting the elution product containing nucleic acid, to make the solution suitable for e.g. PCR. Preferably the present invention substantially avoids diluting the released nucleic acid.

Preferably the step of binding DNA occurs under mild conditions, suitably at a pH of no less than 3.0, preferably no less than 3.5, 4.0, 4.5 or 5.0. Previous methods have used high concentrations of chaotropic agents, such as 8M guanidine. Such conditions may not be necessary in the practice of the present invention, in which the binding step preferably occurs in solution having a total concentration of 1M or less. More preferred temperatures and ionic strengths are as detailed above for the releasing step.

The use of such mild conditions for the release of nucleic acid is especially useful for extracting small quantities of nucleic acid, as the extracted DNA or RNA can be added directly to a reaction or storage tube without further purification steps (e.g. steps necessitated by the use of high ion concentrations in prior art methods), and without the need to dilute high ionic strength (as is the case with prior art methods using high ionic strength to elute the nucleic acid). Therefore loss of nucleic acid through changing the container, imperfect recovery during purification steps, degradation, or denaturation, and dilution of small amounts of nucleic acid can be avoided. This is particularly advantageous when a nucleic acid of interest is present in a sample (or is expected to be present) at a low copy number, such as in certain detection and/or amplification methods.

Broadly speaking, preferred chemical species for use as charge switch materials in accordance with the invention comprise a positively ionisable nitrogen atom, and at least one, but preferably more than one, electronegative group (such as a hydroxy, carboxy, carbonyl, phosphate or sulphonic acid group) or double bond (e.g. C=C double bond), which is sufficiently close to the nitrogen atom to lower its pKa. It has been found that such molecules tend to have suitable pKa values for the extraction of nucleic acid under mild conditions according to the present invention. Preferably at least one (but more preferably more than one) electronegative group is separated from the ionisable nitrogen by no more than two atoms (usually carbon atoms). Hydroxyl groups are particularly preferred electronegative groups (particularly when several hydroxyl groups are present, e.g. in polyhydroxyl amines, such as Tris ($C(CH_2OH)_3$—$NH_2$) or Bis-Tris (see below)), as they (1) lower the pKa of the nitrogen atom (e.g. amine group, e.g. from about 10 or 11) to a suitable value around neutral (i.e. pKa of about 7), (2) allow the species to remain soluble/hydrophilic above the pKa, when the nitrogen atom of the amine group loses its positive charge, (3) provide a site for covalent linkage to a solid substrate, e.g. a polycarboxylated polymer (such as polyacrylic acid), and (4) are uncharged at pH values suitable for the releasing step and at which procedures such as PCR are performed (typically pH 8.5); the presence of charged species can interfere with PCR especially. Especially preferred are chemical species having an ionisable nitrogen atom and at least 2, 3, 4, 5 or 6 hydroxyl groups.

Many standard, weakly basic, buffers are ideal chemical species to provide the ionisable groups of charge switch materials, as they have pKa values close to neutral (i.e. 7).

For use as a charge switch material, chemical species comprising ionisable groups can be immobilized onto solid supports (e.g. beads, particles, tubes, wells, probes, dipsticks, pipette tips, slides, fibers, membranes, papers, celluloses, agaroses, glass or plastics) in a monomeric or polymeric form via adsorption, ionic or covalent interactions, or by covalent attachment to a polymer backbone which is in turn immobilised onto the solid support. Alternatively, they can be incorporated into solid, insoluble forms (with or without attachment to a polymer backbone) which inherently exhibit charge switching, e.g. beads, particles, tubes, wells, probes, dipsticks, pipette tips, slides, fibers, membranes or plastics.

Solid phase materials, especially beads and particles, may be magnetisable, magnetic or paramagnetic. This can aid removal of the solid phase from a solution containing the released nucleic acid, prior to further processing or storage of the nucleic acid.

Preferably the weakly basic buffers are biological buffers, i.e. buffers from the class of buffers commonly used in biological buffer solutions. Examples of biological buffers may be found in commercial chemical catalogues, such as the Sigma catalogue.

Leaching (i.e. transfer from the solid phase into solution in the liquid phase) of chemical species used to provide ionisable groups in ion exchange resins is a virtually inevitable phenomenon to some extent, especially when the species are attached to the solid phase by adsorption. Such leaching typically causes impurity in the resultant product, which can lead to significant problems, particularly if the resultant product is intended to be used in PCR (and especially when the species are charged). The use of biological buffers to provide the ionisable groups in charge switch materials can avoid this problem, since leaching of such buffers into the liquid phase will generally not significantly affect the nucleic acid, nor any downstream processes such as PCR to which it might be subjected. Indeed, many biological buffers are routinely used in PCR buffers, storage buffers and other buffer solutions.

In a particularly preferred embodiment, the releasing step takes place in a buffer solution containing the same biological buffer that is used in, as or on the charge switch material.

Examples of suitable biological buffers for use in charge switch materials in accordance with the invention, and their pKa values, are as follows:

N-2-acetamido-2-aminoethanesulfonic acid ‡‡ (ACES), pKa 6.8;
N-2-acetamido-2-iminodiacetic acid ‡‡ (ADA), pKa 6.6;
amino methyl propanediol † (AMP), pKa 8.8;
3-1,1-dimethyl-2-hydroxyethylamino-2-hydroxy propanesulfonic acid † (AMPSO), pKa 9.0;
N,N-bis2-hydroxyethyl-2-aminoethanesulfonic acid †† (BES), pKa 7.1;
N,N-bis-2-hydroxyethylglycine † (BICINE), pKa 8.3;
bis-2-hydroxyethyliminotrishydroxymethylmethane ‡‡ (Bis-Tris), pKa 6.5;
1,3-bistrishydroxymethylmethylaminopropane ‡‡ (BIS-TRIS Propane), pKa 6.8;
4-cyclohexylamino-1-butane sulfonic acid (CABS), pKa 10.7;
3-cyclohexylamino-1-propane sulfonic acid (CAPS), pKa 10.4;
3-cyclohexylamino-2-hydroxy-1-propane sulfonic acid (CAPSO), pKa 9.6;
2-N-cyclohexylaminoethanesulfonic acid (CHES) pKa 9.6;
3-N,N-bis-2-hydroxyethylamino-2-hydroxypropanesulfonic acid †† (DIPSO), pKa 7.6;
N-2-hydroxyethylpiperazine-N-3-propanesulfonic acid †† (EPPS or HEPPS), pKa 8.0;
N-2-hydroxyethylpiperazine-N-4-butanesulfonic acid † (HEPBS), pKa 8.3;
N-2-hydroxyethylpiperazine-N-2-ethanesulfonic acid †† (HEPES), pKa 7.5;
N-2-hydroxyethylpiperazine-N-2-propanesulfonic acid †† (HEPPSO), pKa 7.8;
2-N-morpholinoethanesulfonic acid ‡ (MES), pKa 6.1;
4-N-morpholinobutanesulfonic acid †† (MOBS), pKa 7.6;
3-N-morpholinopropanesulfonic acid †† (MOPS), pKa 7.2;
3-N-morpholino-2-hydroxypropanesulfonic acid ‡‡ (MOPSO), pKa 6.9;
piperazine-N-N-bis-2-ethanesulfonic acid ‡‡ (PIPES), pKa 6.8;
piperazine-N-N-bis-2-hydroxypropanesulfonic acid †† (POPSO), pKa 7.8;
N-trishydroxymethyl-methyl-4-aminobutanesulfonic acid † (TABS), pKA 8.9;
N-trishydroxymethyl-methyl-3-aminopropanesulfonic acid †† (TAPS), pKa 8.4;
3-N-trishydroxymethyl-methylamino-2-hydroxypropanesulfonic acid †† (TAPSO), pKa 7.4;
N-trishydroxymethyl-methyl-2-aminoethanesulfonic acid †† (TES), pKa 7.4;
N-trishydroxymethylmethylglycine † (TRICINE), pKa 8.1; and
trishydroxymethylaminomethane † (TRIS), pKa 8.1;
histidine*, pKa 6.0, and polyhistidine ‡‡;
imidazole*, pKa 6.9, and derivatives* thereof (i.e. imidazoles), especially derivatives containing hydroxyl groups**;
triethanolamine dimers, oligomers and polymers**; and
di/tri/oligo amino acids**, for example Gly-Gly, pKa 8.2; and Ser-Ser, Gly-Gly-Gly, and Ser-Gly, the latter three having pKa values in the range 7–9.

In a preferred embodiment, the buffers marked above with an asterisk (*) are not considered to be biological buffers for the purposes of the invention (whether or not they are designated as such in any chemical catalogue). In a more preferred embodiment, those marked with two asterisks (**) are also not considered to be biological buffers. Preferred biological buffers are marked with a dagger (†), more preferred buffers are marked with two daggers (††), still more preferred buffers are marked with a double dagger (‡) and most preferred buffers are marked with two double daggers (‡‡).

These and other chemical species comprising ionisable groups may be coated as monomers onto a solid phase support using covalent, ionic or adsorption interactions. Additionally or alternatively, they may be coated onto such solid phase supports in polymeric form (preferably following condensation polymerisation), for example by adsorption onto a negatively charged surface (e.g. a surface having exposed COOH or $SO_3$ groups), or by covalent attachment. Additionally or alternatively, the chemical species containing ionisable groups may be attached to a polymer (see below) which is then attached to a solid support, e.g. by adsorption or covalent attachment.

Preferably the chemical species or polymer backbones are covalently coupled to the solid support via a hydroxyl group or other group so that the ionisable group having the desired pKa value (usually, but not limited to, a nitrogen atom) remains capable of binding and releasing nucleic acid.

Biological buffers and other chemical species comprising positively ionisable groups may be used in conjunction with a chemical species containing a negatively ionisable group which has a suitable pKa, preferably in the ranges described above. For example a biological buffer (having one or more positively ionisable nitrogen atoms) may be attached to a polymer or other solid phase material which has exposed carboxy groups even after attachment of the biological buffer. Such a material may bind nucleic acids at a low pH when few of the carboxy groups are negatively charged (i.e. few are in the $COO^-$ form, most being in the COOH form) and most of the ionisable nitrogen atoms are positively charged. At higher pH the negative charge is stronger (i.e. a greater proportion of carboxy groups are in the $COO^-$ form) and/or the positive charge is weaker, and the nucleic acid is repelled from the solid phase.

Chemical species containing ionisable groups (such as the biological buffers listed above) can be attached to a polymer backbone using known chemistries. For example a chemical species containing a hydroxyl group can be attached using carbodiimide chemistry to a carboxylated polymer backbones. Other chemistries include can be employed by someone skilled in the art using other polymer backbones (e.g. based on polyethylene glycol (PEG) or carbohydrate) using a range of standard coupling chemistries (see e.g. Immobilised Affinity Ligand Techniques, Greg T. Hermanson, A. Krishna Mallia and Paul K. Smith, Academic Press, Inc., San Diego, Calif., 1992, ISBN 0123423309, which is incorporated herein by reference in its entirety.)

Alternatively, the chemical species containing ionisable groups can be polymerised without a backbone polymer, using cross-linking agents, for example reagents that couple via a hydroxy group (e.g. carbonyldiimidazole, butanediol diglycidyl ether, dialdehydes, diisothiocyanates). Polymers may also be formed by simple condensation chemistries to generate polymeric amino acids with the appropriate pKa e.g. Gly-Gly.

Preferably such immobilisation, attachment and/or polymerisation of the chemical species containing the ionisable group does not affect the pKa of the ionisable group, or leaves it in the desired ranges given above. For example it is generally preferred not to couple or polymerize the chemical species via a positively ionisable nitrogen atom (in constrast for example to WO97/2982). In the practice of the invention, it is especially preferred to immobilise, attach and/or polymerise the chemical species via an hydroxyl group.

A preferred polymeric material is a dimer or oligomer of Bis-Tris, or a material formed by attaching a plurality of Bis-Tris molecules to a polyacrylic acid backbone, e.g. by reacting Bis-Tris monomer with polyacrylic acid using 1-ethyl-3-dimethylaminopropyl carbodiimide (EDC). The polymer can then be easily separated from the reactants using dialysis against a suitable reagent or water. Preferably the polyacrylic acid has molecular weight of between about 500 and 5 million or more. More preferably it has a molecular weight of between 100,000 and 500,000.

The nature of the resultant Bis-Tris/polyacrylic acid molecule will depend on the ratio of the coupled components, since the polymer will have different properties depending on the proportion of the acrylic acid groups that are modified with Bis-Tris, for example it is desirable for some carboxy groups to remain unmodified, as the presence of these will not prevent the Bis-Tris from binding nucleic acid at low pH (especially if the Bis-Tris is in excess), but their negative charge at higher pHs will assist with release of the nucleic acid. For use in the present invention, the molar ratio of Bis-Tris:carboxy groups (before attachment) is preferably between 5:1 and 1:5, more preferably between 3:1 and 1:3, still more preferably between 2:1 and 1:2, further preferably between 1.5:1 and 1:1.5, and most preferably about 1:1.

The presence of high residual charge (i.e. charged species present in solution along with the extracted nucleic acid) may adversely affect the analysis of nucleic acids by PCR, or interfere with the binding of primers, dNTPs or polymerase to the nucleic acid, or to the sequestration of $Mg^{2+}$ ions, which are essential to PCR. It is particularly preferable to avoid residual positive charge.

Preferred materials for use in the invention, such as the biological buffers described above, possess minimal residual positive charge (preferably minimal residual charge) at the pH at which the nucleic acid is released, and/or at pHs 8–8.5, making interference with or inhibition of downstream processes unlikely.

Patent application PCT/GB00/02211, of the same inventor, discloses certain methods within the scope of the present invention and is incorporated herein by reference in its entirety as exemplification of the present invention (in all its aspects—see below for other aspects of the invention). In particular, it discloses a method for the extraction of biomolecules from biological material which method comprises contacting the biological material with a solid phase which incorporates histidine or a polyhistidine which will tend to bind nucleic acids at low pH and then extracting the biomolecules bound to the solid phase by elution using an elution solvent which will then release the bound nucleic acids when the pH is increased.

An alternative embodiment of the present invention uses a material which is positively charged across a wide pH range, such as 0–12 or 0–14 (e.g. an electropositive substance such as a metal oxide, metal, strong or weak base, which lacks a pKa value, or for which the pKa value is at an extreme of high pH. Such a positively charged material is combined with negatively ionisable material having a pKa intermediate between the pH values at which it is desired to bind and release nucleic acid, or slightly below the pH at which it is desired to bind nucleic acid. This combination of materials allows nucleic acid to be bound at certain pH values, around and below the pKa of the negatively ionisable material, when there are fewer negatively charged groups, but allows the nucleic acid to be released when the pH is increased and a greater number of the ionisable groups are negatively charged. For example, the combination of iron II,III oxide and polycarboxylates (see Examples) binds nucleic acid at pH 4, when a relative scarcity of negative charges allowing the positively charged iron oxides to bind the nucleic acid. When the pH is increased to around 8, a large proportion of the carboxy groups become negatively charged and, despite the remaining presence of positive charges on the iron oxides, the reduction in overall positive charge allows the nucleic acid to be released.

Further examples of charge switching molecules for nucleic acid purification are based on detergents or surfactants that have a hydrophobic portion and a hydrophilic portion which comprises a positively ionisable group with a suitable pKa, e.g. decyl methyl imidazole or dodecyl-Bis-Tris. These detergents/surfactants can be adsorbed onto surfaces e.g. plastic via their hydrophobic portions and the hydrophilic (ionisable) portions can be used to capture nucleic acid.

Another family of suitable materials for capture and easy release of nucleic acids are carbohydrates e.g. glucosamine, polyglucosamine (including chitosans), kanamycins and their derivatives i.e. sugar ring based structures containing one or more nitrogen atoms surrounded by hydroxyl groups which may also contain other groups such as acetate or sulphate groups to provide a suitable pKa for binding and release of nucleic acids.

Another group of materials with suitable pKa values are nucleic acid bases, e.g. cytidine (pKa 4.2). These can be immobilised via hydroxy groups to a polymer or solid phase carboxy group using carbodiimides.

A still further group of materials having members with suitable pKa values are heterocyclic nitrogen-containing compounds. Such compounds may be aromatic or aliphatic and may be monomers, oligomers or polymers, such as morpholine-, pyrrole-, pyrrolidine-, pyridine-, pyridinol-, pyridone-, pyrroline-, pyrazole-, pyridazine-, pyrazine-, piperidone-, piperidine-, or piperazine-containing compounds, e.g. polyvinylpyridine. Such compounds may be substituted with electronegative groups to bring the pKa value(s) of the ionisable nitrogen atom(s) into an acceptable range, e.g. as defined above. However, in some compounds this may not be necessary, the pKa already being in such a range.

Preferred materials for use in accordance with the invention are hydrophilic, for example comprising charge switch materials which are (or which comprise chemical species which before immobilisation or polymerisation are) water soluble.

Once a suitable solid phase has been prepared, comprising a charge switch material, repeated capture and release of nucleic acids can be performed by adjusting the pH up or down. Thus sequential reactions or analysis can be performed on the nucleic acids using the same solid phase. For example, DNA can be isolated from a biological sample using a PCR tube comprising a charge switch material. Then, following PCR, the amplified DNA product may be isolated from the buffer constituents or primers by adjusting the pH in the same tube.

Particularly preferred solid phase materials are non-porous. Porous supports are commonly used for isolating proteins, which can be trapped in the pores of the support. However, nucleic acids tend to be too big to enter into pores of commonly used such supports, and will therefore become bound to the surface of the support, potentially trapping impurities in the pores.

The method can be used to separate single stranded RNA or DNA from double stranded DNA, because of the different charge densities on single and double stranded molecules, by appropriate manipulation of the pH or salt concentration. Typically, single stranded molecules will be released from binding to the solid phase at a lower pH than double stranded molecules.

In some circumstances, for example for the construction of gene chips, and for the preparation of probes, it may be desirable to produce single stranded DNA. Manipulation of pH and/or ionic strength can assist in purification and release of single stranded nucleic acid. The method of the invention may comprise a prior step of converting double stranded nucleic acid in the sample to single stranded nucleic acid (preferably using a strong base, e.g. 100 mM NaOH, or a weak base at high temperature, e.g. 60–100° C.). The solid phase material is preferably then added simultaneously with a buffer which changes the pH of the sample to the pH for binding single stranded nucleic acid (typically a pH of 4–7).

The materials described herein may also be employed to capture nucleic acids in the liquid phase where binding leads to a cross-linked lattice large enough to separated from the liquid phase, e.g. by filtration or centrifugation.

Accordingly, in a second aspect, the present invention provides a method for extracting nucleic acid from a sample containing nucleic acids, which method comprises: contacting the sample with a charge switch material at a first pH at which the charge switch material has a positive charge and will bind negatively charged nucleic acid; and then releasing the nucleic acid at a second, higher pH at which the charge is neutral, negative or less positive than at the first pH, wherein the charge switch material is soluble at said first pH, and wherein the combination of the charge switch material and the bound nucleic acid is insoluble at or above said first pH and below said second pH.

Preferred features of the method are as set out above, with the exception of the charge switch material being formed into, immobilised on, or attached to, a solid phase material.

Usually the charge switch materials will be soluble at the second pH, and will remain in solution with the nucleic acid upon release of the nucleic acid; the use of a weakly basic buffer (optionally bound to a soluble backbone, e.g. polyacrylic acid) as the charge switch material can avoid problems of contamination as described above.

The methods of the invention preferably include one or more washing steps between the binding and releasing steps. Such (a) washing step(s) will generally be carried out at said first pH, or a pH above said first pH but lower then said second pH, such that the nucleic acid is substantially not released during the washing step(s).

As has been indicated previously, the methods of the invention are particularly suitable for extracting nucleic acid which is then stored or further processed (e.g. by PCR), particularly when the charge switch material is in the form of e.g. a tube or well in which such storage and/or processing can occur. For the avoidance of doubt, however, it is emphasised that the releasing step and any subsequent storage or processing need not be carried out as discrete steps, but can coincide, when said storage or processing occurs at a pH at which release of the nucleic acid occurs. For example, the method of the invention includes binding nucleic acid to a charge switch material coated on or otherwise provided by a PCR tube, washing the bound nucleic acid, and then without a separate releasing step commencing the PCR reaction using a PCR buffer which causes release of the nucleic acid.

In a further aspect, the present invention provides novel charge switch materials for use in the methods of the receding aspects. It further comprises the use of such charge switch materials in such methods. All preferred features of the charge switch materials described in above in the context of the methods apply equally and independently to the present aspect of the invention (i.e. preferred combinations of features may be different in relation to this aspect from the preferred combinations in relation to the method aspects).

In a further aspect, the present invention provides a container (preferably a PCR or storage tube or well, or a pipette tip) coated with, comprising or formed from a charge switch material, preferably a charge switch material comprising a biological buffer.

The following description is directed particularly to the extraction of nucleic acid from blood, but applies also to the extraction of nucleic acid from any liquid sample, particularly biological samples or samples produced during laboratory techniques, such as PCR.

The method is particularly useful if the biological material is blood, but the method can be used for a range of applications substances such as plasmid and vector isolation and plant DNA extraction.

Preferably the cells in the blood are lysed to release nucleic acids and known lysing agents and methods can be used, such as contacting with ionic and non ionic detergents, hypotonic solutions of salts, proteases, chaotropic agents, solvents, using pH changes or heat. A method of lysing cells to isolate nucleic acid is described in WO 96/00228.

When the biological material consists of blood the samples can optionally be diluted with water or other diluent in order to make it easier to manipulate and to process.

Dilutions up to ten times can be used and in general more dilution can be better and it is a feature of the present invention that it allows low dilution of blood to be possible.

The solid phase with which the blood is contacted, can be a formed of a material which has a natural affinity for nucleic acids or it can be formed of a material which has its surface treated with an agent which will cause nucleic acids to bind to it or increase its affinity for nucleic acids. Suitable materials include controlled pore glass, polysaccharide (agarose or cellulose), other types of silica/glass, ceramic materials, porous plastic materials such as porous plastic plugs which in a single moulded part or as an insert in a standard tube, polystyrene beads para magnetic beads etc. The size and porosity is not critical and can vary and be selected for particular applications.

Suitable means for treating the surface of the solid phase or for derivatising it include treating it with a substance which can introduce a charge e.g. a positive charge on the surface or a hydrophilic or hydrophobic surface on the solid phase e.g. hydroxyl groups, nitrate groups, autoreactive groups, dyes and other aromatic compounds.

In a preferred embodiment of the invention the solid phase will cause DNA to be bound to it at one pH in preference to contaminants in the blood sample and will allow the bound nucleic acid to be released when it is contacted with an eluant at a different pH. This system can be used with a solid phase which incorporates histidine or a polyhistidine which will tend to bind nucleic acids at low pH e.g. less than 6 and will then release the bound nucleic acids when the pH is increased e.g. to greater than 8. Alternatively the nucleic acids are bound at substantially neutral pH to an aminated surface and released at very high pH.

In another embodiment of the invention a plastic moulding can incorporate a binding agent e.g. in a well in a plate etc. so that the binding agent is incorporated in the surface, the blood sample is then contacted with the surface so as to cause nucleic acids to be bound to the surface. The blood sample is then removed and the surface treated with an eluting agent to release the bound nucleic acids. When the surface is part of a well in a multi-well plate, the total system can be readily adapted for rapid large scale sampling and extraction techniques.

Binding agents which can be used include charge switchable ion exchange resins using a positively charged solid phase that can be reversed or made neutral by changing the pH above its pKa. e.g. nucleotides, polyamines, imidazole groups and other similar reagents with a suitable pKa value.

Also, nucleic acids can be bound by intercalation using a variety of intercalating compounds incorporated into the solid phase e.g. actinomycin D, ethidium bromide etc.

In a further embodiment of the invention a plastic surface can be modified to include functional groups. The plastic can be any plastic used for containing samples e.g. polypropylene. The functional groups can be positively or negatively charged so as to bind the nucleic acids in the correct buffer solution.

Alternatively the functional groups can be chemical groups capable of covalent coupling to other ligands or polymers.

When the plastic is used in a plastic moulding e.g. in a well in a plate, or as a polymerase chain reaction (PCR) tube, the surface characteristics of the plastic can be suitably modified for use in the present invention by including or adding the appropriate chemicals in the moulding compound e.g. as in an injection moulding compound.

When this is used in a PCR tube or in a deep well plate the tubes or wells can be used to isolate and imobilise small quantities of DNA or RNA generating a pure template for subsequent PCR or other genetic analysis and manipulation.

When the plastic is polypropylene e.g. it is in the form of a thin walled PCR tube the polypropylene surface can be modified by oxidising the surface with an oxidising agent such as potassium permanganate and sulphuric acid to create a carboxylated surface (COOH groups). This tube can then be used to improve the isolation of DNA from solutions or from crude samples e.g. blood. By adjusting the pH, di-electric constant, solubility or ionic strength the DNA or RNA can be immobilised on the walls of the tube, washed free of contaminants, ready for PCR or other analytical techniques.

The carboxy groups can be further modified by covalently coupling an anionic group such as imidazole or polyhistidine or any strong or weak ion exchanger, to allow binding of nucleic acids by a charge interaction. This tube could then be used to improve the isolation of DNA from solutions or from crude samples e.g. of blood. Again by adjusting the pH, di-electric constant, or ionic strength the DNA or RNA can be immobilized on the walls of the tube, washed free of contaminants, ready for PCR or other analytical techniques.

The nucleic acids can be eluted with in a low salt buffer so that it is ready for PCR or other analysis.

The solid phase can be contacted with a blood sample by mixing with the solid phase in a mixing/stirring device, by passing the blood sample over the solid phase or the solid phase can be paramagnetic and manipulated by a magnetic field. Although the invention is particularly suitable for the separation or isolation of nucleic acids from blood it can be used with a range of biomolecules particularly those that require removal of cell wall debris or insoluble particles.

In a preferred embodiment of the invention the solid phase is in granular form in a column and the blood sample is drawn up through the column by means of a pressure differential being applied through the column, the blood sample is drawn up with air and the granular solid material can become fluidised thus increasing the mixing and contacting rates and minimising clogging.

The method of the invention is suitable for use in a multi-well format when a series of extractions from different samples can take place substantially simultaneously and this will facilitate the automation of the extraction process allowing rapid high throughput extraction to take place and to allow combinational chemistry to be performed. This will enable there to be a high throughput in a standard well array e.g. an eight by twelve array so that a large number of sample types can be treated automatically at the same time.

The invention, in its various aspects, will now be described in detail, by way of example only.

EXAMPLE 1

Extraction of Nucleic Acids from Whole Blood

A charge switchable ion-exchanger was prepared by covalently coupling polyhistidine to 100 μm glass beads using glutaldehyde by mixing 1 gram of the aminated glass beads with 0.01% (v/v) glutaldehyde in 0.1M sodium bicarbonate at pH8 containing 20 mg polyhistidine. After overnight incubation the beads were washed exhaustively to remove non-covalently bound material and stored in 10 mM MES, pH5 containing 0.1% (v/v) Tween 20.

About 300 mg of the 100 μm derivitised glass beads were added to a 1 ml plastic column enclosed at both ends.

A blood sample was incubated with an equal volume of 10 mM MES pH5, containing 1% Tween 20, proteases (200 μg/ml) and 1 mM EDTA.

After digestion is complete the blood was sucked up the column containing the glass beads and the DNA became immobilised allowing the contaminating proteins to pass through to waste.

The glass beads containing the immobilised DNA were washed with a buffer comprising 10 mM MES pH5, containing 1% Tween 20, and 1 mM EDTA and this was repeated until the wash solution was colourless.

After washing, the beads were dried with air and DNA eluted with a small quantity of 10 mM Tris HCl, pH 8.5 and collected in a sterile tube ready for analysis. Thus the DNA were separated from the blood.

For different biomolecules, the buffer etc. can be suitably modified.

EXAMPLE 2

One gram of carboxylated paramagnetic beads were washed in 50 mM Imidazole buffer pH6 and then mixed with 100 mg of polyhistidine in 50 ml of 50 mM Imidazole buffer pH 6. A chemical coupling agent was added (EDC) at a final concentration of 5 mg per ml and mixed overnight. The beads were washed in water, 0.5M sodium chloride, 1% Tween 20, 100 mM Tris HCl pH 8 and stored in 10 mM MES, 0.1% Tween 20 pH5.

To extract DNA from blood, 1 mg of beads were mixed with blood diluted in 10% Tween 20 with 25 mM MES, 1 mM EDTA pH 5. The beads were separated with a magnet and washed by resuspending in 1 mM MES, 0.1% Tween 20. To elute the DNA the beads were resuspended in 10 mM Tris HCl pH 8.5 and separated with magnet leaving the DNA in solution.

EXAMPLE 3

Bis-Tris Solid Phase Magnetic Beads 200 mg of carboxylated 1 μm magnetic particles were reacted in a one step procedure with 100 mg of Bis-Tris and 100 mg of the carbodiimide, EDC, in 50 mM imidazole buffer pH6.0. Following an overnight incubation, the magnetic particles were washed and used to isolate Plasmid DNA.

An alkaline lysis method was used to prepare a cleared 5 ml bacterial lysate generating a supernatant containing the plasmid in 0.5M potassium acetate, pH5. To the supernatant, 2.5 mg of magnetic particles were added and mixed for 1 minute. After magnetic separation and washing with water pH5, the pure plasmid DNA was eluted off in 200 μl of 10 mM Tris.HCl pH 8.5.

The magnetic beads were also used to extract DNA directly from whole blood using a detergent based digestion reagent containing proteinase K.

EXAMPLE 4

Tricine on Solid Phase Magnetic Beads 50 mg of carboxylated 1 μm magnetic particles were reacted in a one step procedure with 50 mg of Tricine and 100 mg of the carbodiimide, EDC, in 50 mM imidazole buffer pH6.0. Following an overnight incubation, the magnetic particles were washed and used to isolate Plasmid DNA. An alkaline lysis method was used to prepare a cleared 5 ml bacterial lysate generating a supernatant containing the plasmid in 0.5M potassium acetate, pH5. To the supernatant, 2.5 mg of magnetic particles were added and mixed for 1 minute. After magnetic separation and washing with water pH5, the pure nucleic acids were eluted off in 200 μl of 10 mM Tris.HCl pH 8.5.

EXAMPLE 5

Bis-Tris Solid Phase Polystyrene Beads 1 gram of carboxylated 60 μm polystyrene particles were reacted in a one step procedure with 500 mg of Bis-Tris and 500 mg of the carbodiimide, EDC, in 50 mM imidazole buffer pH6.0. Following an overnight incubation, the particles were washed and used to isolate plasmid nucleic acids as described above.

EXAMPLE 6

Bis-Tris Polymer

Bis-Tris monomer was converted into a polymer by mixing together 160 mg of polyacrylic acid with a molecular weight of 240,000, 1.6 g of Bis-Tris and 1.6 g of EDC in 50 mM imidazole pH6.0. Following an overnight incubation, the mixture was dialysed in water. The purified polymer was then coated onto magnetic COOH beads or used in the liquid phase to bind genomic DNA from blood. A 5 ml blood sample was centrifuged to obtain the nuclei and WBC population and the resulting pellet digested with 1% SDS. Following precipitation with potassium acetate the cleared supernatant was mixed with either 25 mg of magnetic-Bis-Tris or about 250 μg of poly-Bis-Tris as a liquid. In both cases the captured DNA could be separated, washed in water and then redissolved in 10 mM Tris HCl pH8.5 in a pure form.

EXAMPLE 7

Insoluble Tris HCl Polymer

In this example an insoluble polymer was made with inherent charge switching properties by mixing 80 mg of polyacrylic acid with 800 mg of Tris HCl and 800 mg of EDC in 50 mM Imidazole pH6. The insoluble precipitate that formed generated a particulate solid phase that was used to capture DNA and release it in a similar manner to that described in example 4 for genomic DNA.

EXAMPLE 8

Immobilised Poly Bis-Tris on Tips

A solution of poly Bis-Tris at 1 mg/ml, prepared as in Example 2, in 0.1M sodium bicarbonate pH8 incubated at 60° C. for 8 hours with twenty 200 µl polyproplylene pipette tips. The tips were then rinsed and used to capture about 150 ng of plasmid DNA from a cleared bacterial lysate by pumping up and down ten times. After a quick wash with water pH5, the DNA was eluted in 50 µl of 10 mM Tris pH 8.5.

EXAMPLE 9

Immobilised Poly Bis-Tris on PCR Tubes

A solution of poly Bis-Tris at 1 mg/ml, prepared as in Example 2, in 0.1M sodium bicarbonate pH8 incubated at 60° C. for 8 hours in a 200 ul PCR plate of 8×12 tubes. After rinsing, the tubes were used to bind genomic DNA from a sample prepared according to example 4. About 50 ng of DNA was subsequently eluted off per tube using 10 mM Tris HCl pH8.5.

EXAMPLE 10

Charge Switch Detergents in Liquid Phase

A blood sample was prepared as described in Example 4 and to the resulting supernatant decyl imidazole was added at pH 4 causing precipitation of the DNA. The DNA pellet was collected by centrifugation and redissolved in 10 mM Tris pH 8.5.

EXAMPLE 11

Charge Switch Detergents on Solid Phase

Decyl imidazole was adsorbed onto a 200 ul plastic pipette tip by soaking in a 1% solution at pH4 in 0.1M sodium acetate. A blood sample was prepared as described in Example 3 and the tips were used to bind the DNA by repeated pumping and sucking. After a wash with water, about 50 ng of DNA was recovered in water at pH10.

EXAMPLE 12

Polyglucosamines 10 mg of low molecular weight Chitosan was dissolved in acidified water and then 50 mM imidazole pH5.5, this was mixed with 100 mg of carboxy 1 µm magnetic beads and with 20 mg of the carbodiimide EDC in 50 mM imidazole pH5.5. Following an overnight incubation, the beads were washed and resuspended in 10 mM MES pH5. To bind genomic DNA, 2 mg of magnetic particles were added to a supernatant prepared by methods described earlier in Example 1, after magnetic separation, the DNA was eluted using 100 mM Tris.HCl pH 9.5.

EXAMPLE 13

Kanamycin

A solution of genomic DNA was prepared as described in example 3. To this sample 2 mg of Kanmycin was added at a concentration of 10 mg/ml. The resulting precipitate of DNA was filtered, washed in water at pH5 and re-dissolved in water at pH10.

EXAMPLE 14

Magnetisable Iron Oxides in Carboxylated Polystrene

A 5 ml Plasmid mini-prep was prepared using standard alkaline lysis reagents to generate a cleared lysate with a potassium acetate composition of 0.5M pH4. To this cleared supernatant, 2.5 mg of commercially available 1 µm carboxylated polystyrene magnetisable particles were added to bind the plasmid DNA. The particles were washed with water at pH4 and then the DNA eluted using 10 mM Tris HCl at pH 8.5. Typical UV ratios at 260 and 280 nm were 1.7–2.0, indicating pure nucleic acids with a single band observed with standard gel electrophoresis.

EXAMPLE 15

Titanium Dioxide in Polystyrene Microtitre Plates

A solution of DNA at 100 µg per ml in 0.1M Potassium Acetate pH4 was allowed to stand for 1 hour in a 300 µl flat bottomed microtitre plastic plate, the plastic plate contained titanium oxide which was incorporated as a powder in the plastic when the plate was formed. After washing at pH4, the DNA was recovered with water at pH10 and 2 ml measured at 260 nm versus a plain polystyrene plate with no titanium oxide. Approximately, 50 ng of DNA was recovered per 300 µl well for the plate incorporating the titanium oxide compared to zero for the plain polystyrene plate.

EXAMPLE 16

Cytidine Coupled to Magnetic Beads 1 gram of carboxylated 1 µm magnetic particles were reacted in a one step procedure with 500 mg of Cytidine and 500 mg of the carbodiimide, EDC, in 50 mM imidazole buffer pH6.0. After thorough washing, the beads were used to bind nucleic acids from a plasmid preparation as described in example 1 and recovering the pure nucleic acids in water at pH10.

EXAMPLE 17

Polyvinyl Pyridine (PVP)

20 mg of commercially available PVP beads was mixed with the supernatant containing genomic DNA from a 5 ml blood extraction described in example 4. After allowing the DNA to bind, the beads were washed with water at pH5 and the DNA recovered using water at pH10. Ultra violet analyisis at 260 and 280 nm indicated a purity ratio of 1.65.

EXAMPLE 18

Separation of RNA and DNA

A solution of tRNA and sheared genomic DNA was prepared at 30 µg per ml in 50 mM Potassium acetate buffer pH6.5 with 1M sodium chloride. Approximately 4 mg of magnetic polyhistidine beads were mixed with 1 ml of the nucleic acid solution for one minute until binding was complete. The beads were then thoroughly washed with water at pH5. To elute the bound material, the beads were mixed with 300 µl of 10 mM Tris.HCl, 10 mM NaCl, pH8.5. Gel analysis showed that most of the tRNA remained in solution and was not bound to the beads. The eluted material contained mostly genomic DNA with little or no tRNA.

EXAMPLE 19

DNA Analysis

In all previous examples, extracted DNA was analysed by one or more of the following:
  (1): ultra violet (UV) analysis at 260 nm and 280 nm, to provide a measure of nucleic acid concentration;

(2): Gel electrophoresis using 1% agarose in TBE buffer run at 60V for 20 minutes vs a commercial preparation of DNA as control, with ethidium bromide staining to measure molecular size and to provide an estimate of quantity of the nucleic acid; or (3): PCR using primers specific for actin or other ubiquitous genes, to test integrity of the nucleic acid.

The results are presented as (1): direct readings from the instrument; and (2); and (3): gel pictures.

In all cases, the examples demonstrated effective extraction of nucleic acid which was not significantly damaged.

What is claimed is:

1. A product comprising a solid phase for use in a method in which the solid phase reversibly binds nucleic acid present in a sample, the product comprising a plurality of positively ionizable groups, wherein the ionizable groups are immobilized on the solid phase and are effective at a first pH at which the ionizable groups are positively charged to bind nucleic acid present in a sample and are effective to release the nucleic acid at a second, higher, pH at which the charge on the ionizable groups is negative, neutral or less positive, the ionizable groups being provided by a chemical species selected from the group consisting of biological buffers, polyhydroxylated amines, histidine and polyhistidine, wherein said plurality of positively ionizable groups have a pKa between about 4.5 and about 8.5.

2. A product according to claim 1, wherein the plurality of positively charged groups are provided by a biological buffer which is selected from the group consisting of:

N-2-acetamido-2-aminoethanesulfonic acid (ACES);
N-2-acetamido-2-iminodiacetic acid (ADA);
N,N-bis2-hydroxyethyl-2-aminoethanesulfonic acid (BES);
N,N-bis-2-hydroxyethylglycine (BICINE);
bis-2-hydroxyethyliminotrishydroxymethylmethane (Bis-Tris);
1,3-bistrishydroxymethylmethylaminopropane (Bis-Tris Propane);
3-N,N-bis-2-hydroxyethylamino-2-hydroxypropanesulfonic acid (DIPSO);
-2-hydroxyethylpiperazine-N-3-propanesulfonic acid (EPPS);
-2-hydroxyethylpiperazine-N-4-butanesulfonic acid (HEPBS);
-2-hydroxyethylpiperazine-N-2-ethanesulfonic acid (HEPES);
-2-hydroxyethylpiperazine-N-2-propanesulfonic acid (HEPPSO);
2-N-morpholinoethanesulfonic acid (MES);
4-N--morpholinobutanesulfonic acid (MOBS);
3-N-morpholinopropanesulfonic acid (MOPS);
3-N-morpholino-2-hydroxypropanesulfonic acid (MOPSO);
piperazine-N-N-bis-2-ethanesulfonic acid (PIPES);
piperazine-N-N-bis-2-hydroxypropanesulfonic acid (POPSO);
N-trishydroxymethyl-methyl-3-aminopropanesulfonic acid (TAPS);
3-N-trishydroxymethyl-methylamino-2-hydroxypropanesulfonic acid (TAPSO);
N-trishydroxymethyl-methyl-2-aminoethanesulfonic acid (TES);
N-trishydroxymethylmethylglycine (TRICINE);
trishydroxymethylaminomethane (Tris);
polyhydroxylated imidazoles; and
triethanolamine dimers and polymers.

3. A product according to claim 1, wherein the plurality of ionizable groups are separately immobilised on a solid support by covalent or ionic bonding or by adsorption.

4. A product according to claim 1, wherein the plurality of ionizable groups are separately attached to a polymer, said polymer being immobilised on a solid support by covalent or ionic bonding or by adsorption.

5. A product according to claim 1, wherein the ionizable groups are polymerised, optionally by means of cross-linking reagents.

6. A product according to claim 5, wherein the polymer is immobilised on a solid support by covalent or ionic bonding or by adsorption.

7. A product according to claim 5, wherein the polymer is a solid.

8. A product according to claim 5 which is a container.

9. A container according to claim 8 which is a polymerase chain reaction or storage tube or well, or a pipette tip.

10. A water soluble product for use in a method of extracting nucleic acid from a sample, the product comprising a plurality of positively ionizable groups, the ionizable groups being provided by a biological buffers; wherein the plurality of ionizable groups are (i) separately attached to a polymer or (ii) polymerized, optionally by means of cross-linking reagents or (iii) separately attached to a polymer and polymerized, optimally by means of cross-linking reagents; and wherein said plurality of positively ionizable groups have a pKa between about 4.5 and 8.5 and the biological buffer is selected from the group consisting of:

N-2-acetamido-2-aminoethanesulfonic acid (ACES);
N-2-acetamido-2-iminodiacetic acid (ADA);
N,N-bis2-hydroxyethyl-2-aminoethanesulfonic acid (BES);
N,N-bis-2-hydroxyethylglycine (BICINE);
bis-2-hydroxyethyliminotrishydroxymethylmethane (Bis-Tris);
1,3-bistrishydroxymethylmethylaminopropane (Bis-Tris Propane);
3-N,N-bis-2-hydroxyethylamino-2-hydroxypropanesulfonic acid (DIPSO);
-2-hydroxyethylpiperazine-N-3-propanesulfonic acid (EPPS);
-2-hydroxyethylpiperazine-N-4-butanesulfonic acid (HEPBS);
-2-hydroxyethylpiperazine-N-2-ethanesulfonic acid (HEPES);
-2-hydroxyethylpiperazine-N-2-propanesulfonic acid (HEPPSO);
2-N-morpholinoethanesulfonic acid (MES);
4-N-morpholinobutanesulfonic acid (MOBS);
3-N-morpholinopropanesulfonic acid (MOPS);
3-N-morpholino-2-hydroxypropanesulfonic acid (MOPSO);
piperazine-N-N-bis-2-ethanesulfonic acid (PIPES);
piperazine-N-N-bis-2-hydroxypropanesulfonic acid (POPSO);
N-trishydroxymethyl-methyl-3-aminopropanesulfonic acid (TAPS);
3-N-trishydroxymethyl-methylamino-2-hydroxypropanesulfonic acid (TAPSO);
N-trishydroxymethyl-methyl-2-aminoethanesulfonic acid (TES);
N-trishydroxymethylmethylglycine (TRICINE);
trishydroxymethylaminomethane (Tris);
polyhydroxylated imidazoles; and
triethanolamine dimers and polymers.

11. A product comprising a solid phase for use in which the solid phase reversibly binds nucleic acid present in a sample, the product comprising a plurality of positively ionizable groups, wherein the ionizable groups are immobilised on the solid phase and are capable at a first pH at which the ionizable groups are positively charged of binding nucleic acid present in a sample and are capable of releasing the nucleic acid at a second, higher, pH at which the charge on the ionizable groups is negative, neutral or less positive, wherein said plurality of positively ionizable groups have a pKa between about 4.5 and about 8.5, the ionizable groups being provided by a biological buffer selected from the group consisting of:

N-2-acetamido-2-aminoethanesulfonic acid (ACES);
N-2-acetamido-2-iminodiacetic acid (ADA);
N,N-bis2-hydroxyethyl-2-aminoethanesulfonic acid (BES);
N,N-bis-2-hydroxyethylglycine (BICINE);
bis-2-hydroxyethyliminotrishydroxymethylmethane (Bis-Tris);
1,3-bistrishydroxymethylmethylaminopropane (Bis-Tris Propane);
3-N,N-bis-2-hydroxyethylamino-2-hydroxypropanesulfonic acid (DIPSO);
-2-hydroxyethylpiperazine-N-3-propanesulfonic acid (EPPS);
-2-hydroxyethylpiperazine-N-4-butanesulfonic acid (HEPBS);
-2-hydroxyethylpiperazine-N-2-ethanesulfonic acid (HEPES);
-2-hydroxyethylpiperazine-N-2-propanesulfonic acid (HEPPSO);
2-N-morpholinoethanesulfonic acid (MES);
4-N-morpholinobutanesulfonic acid (MOBS);
3-N-morpholinopropanesulfonic acid (MOPS);
3-N-morpholino-2-hydroxypropanesulfonic acid (MOPSO);
piperazine-N-N-bis-2-ethanesulfonic acid (PIPES);
piperazine-N-N-bis-2-hydroxypropanesulfonic acid (POPSO);
N-trishydroxymethyl-methyl-3-aminopropanesulfonic acid (TAPS);
3-N-trishydroxymethyl-methylamino-2-hydroxypropanesulfonic acid (TAPSO);
N-trishydroxymethyl-methyl-2-aminoethanesulfonic acid (TES);
N-trishydroxymethylmethylglycine (TRICINE);
trishydroxymethylaminomethane (Tris);
polyhydroxylated imidazoles; and
triethanolamine dimers and polymers.

12. A product according to claim 11, wherein the biological buffer is bis-2-hydroxyethyliminotrishydroxymethylmethane (Bis-Tris).

13. A product according to claim 11, wherein the plurality of ionizable groups are separately immobilised on a solid support by covalent or ionic bonding or by adsorption.

14. A product according to claim 11, wherein the plurality of ionizable groups are separately attached to a polymer, said polymer being immobilised on a solid support by covalent or ionic bonding or by adsorption.

15. A product according to claim 11, wherein the ionizable groups are polymerised, optionally by means of cross-linking reagents.

16. A product according to claim 15, wherein the polymer is immobilised on a solid support by covalent or ionic bonding or by adsorption.

17. A product according to claim 11, wherein the solid phase is selected from the group consisting of beads, particles, tubes, wells, probes, dipsticks, pipette tips, slides, fibers, membranes, papers, glass and plastics.

18. A product according to claim 17, wherein the solid phase is magnetic beads.

19. A product according to claim 17, wherein the solid phase is paramagnetic beads.

20. A product comprising a solid phase for use in which the solid phase reversibly binds nucleic acid present in a sample, the product comprising a plurality of positively ionizable groups, wherein the ionizable groups are immobilised on the solid phase and are capable at a first pH at which the ionizable groups are positively charged of binding nucleic acid present in a sample and are capable of releasing the nucleic acid at a second, higher, pH at which the charge on the ionizable groups is negative, neutral or less positive, the ionizable groups being provided by bis-2-hydroxyethyliminotrishydroxymethylmethane (Bis-Tris) and having a pKa between about 4.5 and 8.5.

21. A product according to claim 20, wherein the bis-2-hydroxyethyliminotrishydroxymethylmethane (Bis-Tris) groups are separately immobilised on a solid support by covalent or ionic bonding or by adsorption.

22. A product according to claim 20, wherein the bis-2-hydroxyethyliminotrishydroxymethylmethane (Bis-Tris) groups are separately attached to a polymer, said polymer being immobilised on a solid support by covalent or ionic bonding or by adsorption.

23. A product according to claim 20, wherein the bis-2-hydroxyethyliminotrishydroxymethylmethane (Bis-Tris) is polymerised, optionally by means of cross-linking reagents.

24. A product according to claim 23, wherein the polymer is immobilised on a solid support by covalent or ionic bonding or by adsorption.

25. A product according to claim 20, wherein the solid phase is selected from the group consisting of beads, particles, tubes, wells, probes, dipsticks, pipette tips, slides, fibers, membranes, papers, glass and plastics.

26. A product according to claim 25, wherein the solid phase is magnetic beads.

27. A product according to claim 25, wherein the solid phase is paramagnetic beads.

28. A product comprising a solid phase for use in which the solid phase reversibly binds nucleic acid present in a sample, the product comprising a plurality of positively ionizable groups, wherein the ionizable groups are immobilised on the solid phase and are capable at a first pH at which the ionizable groups are positively charged of binding nucleic acid present in a sample and are capable of releasing the nucleic acid at a second, higher, pH at which the charge on the ionizable groups is negative, neutral or less positive, the ionizable groups being provided by bis-2-hydroxyethyliminotrishydroxymethylmethane (Bis-Tris) and having a pKa between about 4.5 and 8.5. and the solid phase comprises beads.

29. A product according to claim 28, wherein the bis-2-hydroxyethyliminotrishydroxymethylmethane (Bis-Tris) groups are separately immobilised on the beads by covalent or ionic bonding or by adsorption.

30. A product according to claim 28, wherein the bis-2-hydroxyethyliminotrishydroxymethylmethane (Bis-Tris) groups are separately attached to a polymer, said polymer being immobilised on the bead by covalent or ionic bonding or by adsorption.

31. A product according to claim 28, wherein the bis-2-hydroxyethyliminotrishydroxymethylmethane (Bis-Tris) is polymerised, optionally by means of cross-linking reagents.

32. A product according to claim 31, wherein the polymerized Bis-Tris is immobilised on the beads by covalent or ionic bonding or by adsorption.

33. A product according to claim 28, wherein the solid phase is magnetic beads.

34. A product according to claim 28, wherein the solid phase is paramagnetic beads.

35. A product according to claim 1, wherein the solid phase is selected from the group consisting of beads, particles, tubes, wells, probes, dipsticks, pipette tips, slides, fibers, membranes, papers, glass and plastics.

36. A product according to claim 35, wherein the solid phase is magnetic beads.

37. A product according to claim 35, wherein the solid phase is paramagnetic beads.

38. A product according to claim 1, wherein the pKa of the plurality of ionizable groups is between 5.0 and 6.5.

39. A product according to claim 10, wherein the pKa of the plurality of ionizable groups is between 5.0 and 6.5.

40. A product according to claim 11, wherein the pKa of the plurality of ionizable groups is between 5.0 and 6.5.

41. A product according to claim 20, wherein the pKa of the plurality of ionizable groups is between 5.0 and 6.5.

42. A product according to claim 28, wherein the pKa of the plurality of ionizable groups is between 5.0 and 6.5.

* * * * *